United States Patent
Akers (10) Patent No.: US 8,031,825 B2
(45) Date of Patent: Oct. 4, 2011

(54) NON-DESTRUCTIVE TESTING METHOD AND APPARATUS

(75) Inventor: Douglas W. Akers, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 1105 days.

(21) Appl. No.: 11/626,473

(22) Filed: Jan. 24, 2007

(65) Prior Publication Data

US 2007/0211842 A1    Sep. 13, 2007

Related U.S. Application Data

(62) Division of application No. 10/869,794, filed on Jun. 15, 2004, now Pat. No. 8,009,787.

(51) Int. Cl.
*G21G 1/12* (2006.01)

(52) U.S. Cl. ........................ 376/157; 376/156; 250/492.1

(58) Field of Classification Search ................... 376/157, 376/156; 250/492.1
See application file for complete search history.

(56) References Cited

U.S. PATENT DOCUMENTS

| | | | | |
|---|---|---|---|---|
| 3,593,025 A | * | 7/1971 | Grosskreutz | 250/358.1 |
| 4,064,438 A | * | 12/1977 | Alex et al. | 250/308 |
| 4,835,390 A | * | 5/1989 | Blatchley et al. | 250/356.1 |
| 4,897,549 A | * | 1/1990 | Zerda et al. | 250/358.1 |
| 5,530,245 A | * | 6/1996 | Huang | 250/307 |
| 6,208,704 B1 | * | 3/2001 | Lidsky et al. | 376/156 |
| 6,693,277 B2 | * | 2/2004 | Cowan et al. | 250/303 |
| 7,041,508 B2 | * | 5/2006 | Smith | 436/104 |
| 7,231,011 B2 | * | 6/2007 | Akers | 376/157 |

OTHER PUBLICATIONS

Alvarez et al., "Photoneutron Cross Sections for Na-23 and Mg-25", Physical Review C, vol. 4, No. 5, Nov. 1971, pp. 1673-1679.*
Alvarez et al., "Photoneutron Cross Sections for Mn-55 and Co-59", Physical Review C, vol. 20, No. 1, Jul. 1979, pp. 128-138.*
Nuclides and Isotopes, 14th Edition, GE Nuclea Energy, 1989, pp. 4, 5, 20, 23 and 25.*
IAEA Photonuclear Data Library, Mar. 2000, pp. 104, 147, 153.*
Panofsky et al., "The Reaction N-14(gamma, 2n)N-12", Phys. Rev. 87, 543 (1952).*
Marshall, "Properties of (gamma,n) Cross Sections," Phys. Rev. 83, 345 (1951).*

* cited by examiner

*Primary Examiner* — Ricardo Palabrica
(74) *Attorney, Agent, or Firm* — Fennemore Craig, P.C.

(57) ABSTRACT

Non-destructive testing apparatus may comprise a photon source and a source material that emits positrons in response to bombardment of the source material with photons. The source material is positionable adjacent the photon source and a specimen so that when the source material is positioned adjacent the photon source it is exposed to photons produced thereby. When the source material is positioned adjacent the specimen, the specimen is exposed to at least some of the positrons emitted by the source material. A detector system positioned adjacent the specimen detects annihilation gamma rays emitted by the specimen. Another embodiment comprises a neutron source and a source material that emits positrons in response to neutron bombardment.

5 Claims, 3 Drawing Sheets

NON-DESTRUCTIVE TESTING METHOD AND APPARATUS

CROSS-REFERENCE TO RELATED APPLICATIONS

This Application is a Divisional of U.S. application Ser. No. 10/869,794, entitled METHOD AND APPARATUS FOR NON-DESTRUCTIVE TESTING, filed on Jun. 15, 2004.

CONTRACTUAL ORIGIN OF THE INVENTION

The United States Government has certain rights in this invention pursuant to Contract No. DE-AC07-99ID13727, and Contract No. DE-AC07-05ID14517 between the United States Department of Energy and Battelle Energy Alliance, LLC.

TECHNICAL FIELD

This invention relates generally to the testing and evaluation of materials and more specifically to methods and apparatus for performing non-destructive testing of materials using position annihilation.

BACKGROUND

Non-destructive material evaluation refers to any of a wide variety of techniques that may be utilized to examine materials for defects and/or evaluate the materials without requiring that the materials first be destroyed. Such non-destructive material evaluation is advantageous in that all materials or products may be tested for defects. After being evaluated, acceptable (e.g., substantially defect-free or with acceptable defect levels) materials may be placed in service, while the defective materials may be re-worked or scrapped, as may be appropriate. Non-destructive evaluation techniques are also advantageous in that materials already in service may be evaluated or examined in-situ, thereby allowing for the early identification of materials or components that may be subject to in-service failure. The ability to evaluate or examine new or in-service materials has made non-destructive material evaluation techniques of great importance in safety- or failure-sensitive technologies, such as, for example, in aviation and space technologies, as well as in nuclear systems and in power generation systems.

One type of non-destructive evaluation technique, generally referred to as positron annihilation, is particularly promising in that it is theoretically capable of detecting fatigue and other types of damage in metals, composites, and polymers at its earliest stages. While several different positron annihilation techniques exist, as will be described below, all involve the detection of positron annihilation events in order to ascertain certain information about the material or object being tested.

By way of background, complete annihilation of a positron and an electron occurs when both particles collide and their combined mass is converted into energy in the form of two (and occasionally three) photons (e.g., gamma rays). If the positron and the electron are both at rest at the time of annihilation, the two gamma rays are emitted in exactly opposite directions (e.g., 180° apart) in order to satisfy the requirement that momentum be conserved. Each annihilation gamma ray has an energy of about 511 keV, the rest energies of an electron and a positron.

In positron annihilation analysis, the momentum of the electron is related to the environment in which it resides. For example, electron momentum is relatively low in defects in metals or in microcracks in composite materials and polymers) or in large lattice structures. Electron momentum is higher in defect-free or tight lattice structures. One way to determine the momentum of the electron is to measure the degree of broadening of the gamma-ray energy peak in the spectrum around the 511 keV annihilation energy produced by the annihilation event. Alternatively, the momentum of the electron may be derived from the deviation from 180° of the two annihilation gamma rays.

Additional information about the electron density of the material at the site of annihilation may be obtained by determining the average lifetime of the positrons following a known initiation event before they are annihilated. Still other information about the annihilation event may be detected and used to derive additional or supplemental information regarding the material being tested, such as the presence of contaminants or pores within the material. Accordingly, the detection of positrons and the products of annihilation events provide much information relating to defects and other microstructural characteristics of the material or object being tested.

As mentioned above, several different positron annihilation techniques are known. In one type of positron annihilation technique, positrons from a radioactive source (e.g., $^{22}$Na, $^{68}$Ge, or $^{58}$Co) are directed toward the material to be tested. Upon reaching the material, the positrons are rapidly slowed or "thermalized." That is, the positrons rapidly loose most of their kinetic energy by collisions with ions and free electrons present at or near the surface of the material. After being thermalized, the positrons then annihilate with electrons in the material. During the diffusion process, the positrons are repelled by positively-charged nuclei, thus tend to migrate toward defects such as dislocations in the lattice sites where the distances to positively-charged nuclei are greater. In principle, positrons may be trapped at any type of lattice defect having an attractive electronic potential. Most such lattice defects are so-called "open-volume" defects and include, without limitation, vacancies, vacancy clusters, vacancy-impurity complexes, dislocations, grain boundaries, voids, and interfaces. In composite materials or polymers, such open-volume defects may be pores or microcracks.

Positron annihilation techniques utilizing external positron sources suffer from a variety of disadvantages. For example, one type of external positron source is an isotopic source, such as $^{22}$Na, which emits positrons having generally low energies of about 0.5 million electron volts (MeV) or so. Such low energy positrons can only penetrate a short distance, e.g., less than about 10 microns or so, into metallic materials. Such positrons also lose energy in the source material itself. While higher energy positrons (e.g., having energies of about 3 MeV) can be obtained via non-isotopic sources, such as the Pelletron at Lawrence-Livermore Laboratories, such devices are also not without their disadvantages. For example, the positron beams produced by such sources are often relative narrow, thus cannot easily be made to cover larger specimens. In addition, such external positron sources tend to be physically large, which can limit the ability to place the positron source at the appropriate location on the specimen to be tested. This is particularly true if the specimen comprises a fabricated structure (e.g., a wing structure) that comprises small areas or regions that are simply not large enough to accommodate the large external positron source. Consequently, it may be difficult, if not impossible, to effectively test such structures.

SUMMARY OF THE INVENTION

Non-destructive testing apparatus may comprise a photon source and a source material that emits positrons in response to bombardment of the source material with photons. The source material is alternately positionable adjacent the photon source and a specimen. When the source material is positioned adjacent the photon source, the source material is exposed to photons produced by the photon source, which generates positron-producing nuclei within the source material. When the source material is positioned adjacent the specimen, the specimen is exposed to at least some of the positrons being emitted by the source material. A detector system positioned adjacent the specimen detects annihilation gamma rays emitted by the specimen that provide a measure of the microstructure of the specimen.

Another embodiment of the non-destructive testing apparatus comprises a neutron source and a source material that emits positrons in response to bombardment of the source material with neutrons. The source material is alternately positionable adjacent the neutron source and a specimen. When the source material is positioned adjacent the neutron source, the source material is exposed to neutrons produced by the neutron source, which generates positron-producing nuclei within the source material. When the source material is positioned adjacent the specimen, the specimen is exposed to at least some of the positrons emitted by the source material. A detector system positioned adjacent the specimen detects annihilation gamma rays emitted by the specimen.

A non-destructive testing method according to one embodiment of the invention comprises: providing a source material; bombarding the source material with photons so that the source material emits positrons; placing the source material adjacent a specimen to be tested; and detecting annihilation gamma rays emitted by the specimen.

Another embodiment of a non-destructive testing method comprises providing a source material; bombarding the source material with neutrons so that the source material emits positrons; placing the source material adjacent a specimen to be tested; and detecting annihilation gamma rays emitted by the specimen.

BRIEF DESCRIPTION OF THE DRAWING

Illustrative and presently preferred embodiment of the invention are shown in the accompanying drawing in which.

DETAILED DESCRIPTION OF THE PREFERRED EMBODIMENTS

Figure 1:
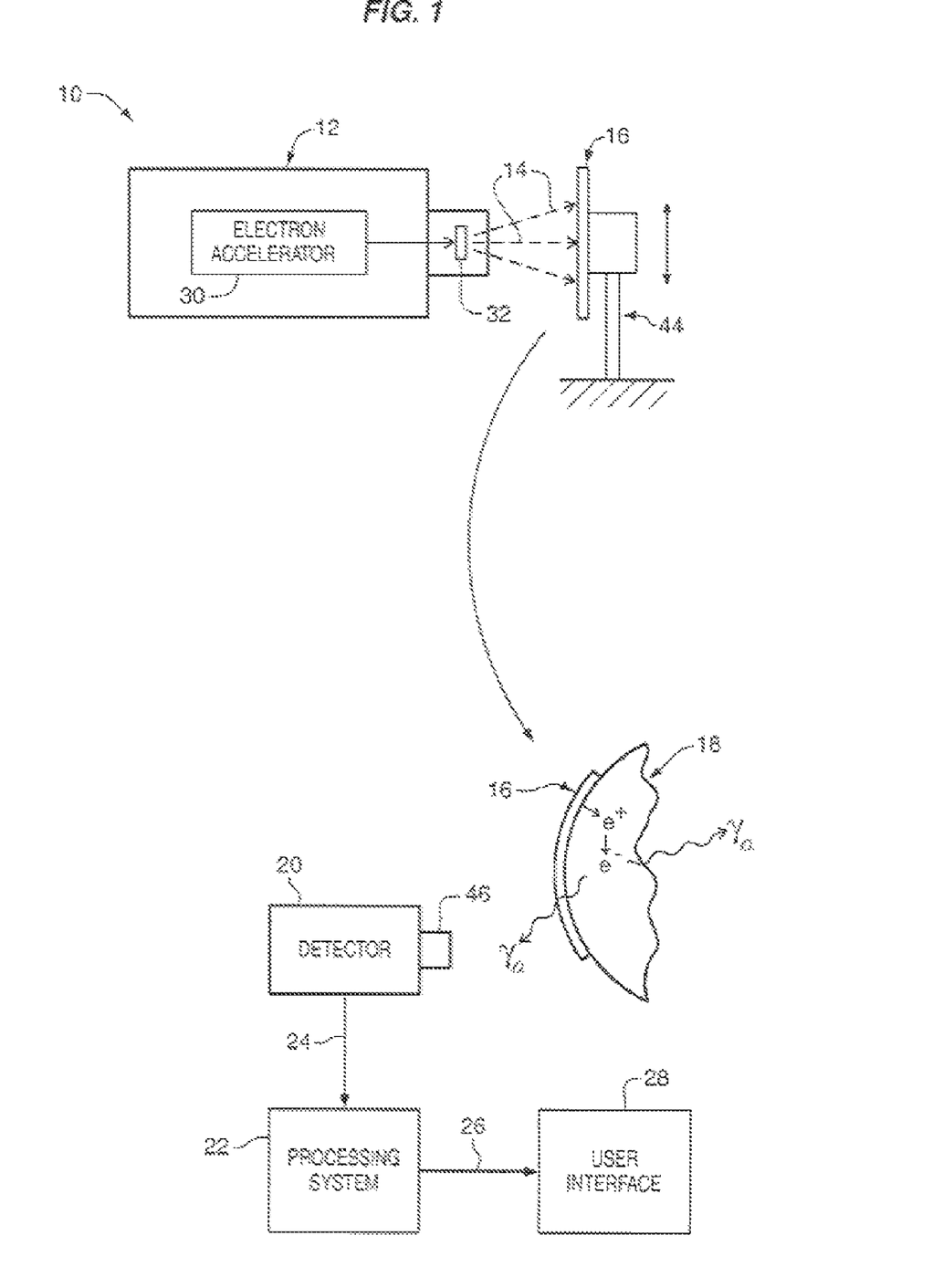
FIG. 1 is a schematic representation of non-destructive testing apparatus according to one embodiment of the present invention.

Non-destructive testing apparatus 10 according to one embodiment of the present invention is illustrated in FIG. 1 and may comprise a photon source 12 for producing photons 14. A source material 16 is positioned adjacent the photon source 12 so that the source material 16 is bombarded by photons 14 from the photon source 12. As will be described in greater detail below, the source material 16 comprises a material that emits positrons $e^+$ in response to bombardment of the source material 16 with photons, such as photons 14 from the photon source 12. After being bombarded with photons 14 from the photon source 12, a process referred to herein in the alternative as "photon activation," the source material 16 may be removed from a position adjacent the photon source 12 and moved to a position adjacent a specimen 18. As will be described in greater detail below, the positrons emitted by the source material 16 may have relatively high energies, e.g., in the range of about 0.5 MeV to about 5 MeV. The higher energies associated with the source material 16 is due in part to the higher energies of the positrons produced within the source material 16. The higher energies are also due in part to the fact that the source material 16 may be made quite thin in comparison with conventional isotopic sources of external positrons, such as $^{22}$Na, thereby resulting in less energy attenuation as the positrons escape the source material 16.

In one embodiment, the source material 16 is conformable (i.e., flexible) so that at least a portion of the source material 16 may be conformed to at least a portion of the specimen 18, as best seen in FIG. 1. The specimen 18 is then exposed to positrons $e^+$ emitted by the source material 16. The ability to place the source material 16 in close proximity to the specimen 18 maximizes the ability to expose the specimen 18 to the high-energy positrons produced by the source material 16. Stated another way, the specimen 18 will be exposed to more positrons and to positrons having higher energies than would be the case if the source material 16 could not be placed in such close proximity to the specimen 18.

At least some of the positrons $e^+$ from the source material 16 penetrate the specimen 18 and annihilate with electrons $e^-$ in the specimen 18. The annihilation of positrons $e^+$ and electrons $e^-$ results in the production or formation of annihilation gamma rays $\gamma_a$ in a process generally known as positron annihilation. The measured annihilation energy plus or minus the momenta of the electrons and positrons provides a measure of the defect density or microcracking that may be present in the specimen 18. A detector 20 positioned adjacent the specimen 18 detects annihilation gamma rays $\gamma_a$ emitted by the specimen 18. A processing system 22 operatively associated with the detector 20 processes output data 24 from the detector and produces output data 26. Thereafter, the output data 26 may be presented on a user interface 28.

A non-destructive testing method according to the present invention may comprise providing a source material 16 that will produce positrons $e^+$ in response to photon bombardment. The source material 16 is then bombarded with photons (e.g., photons 14 from the photon source 12) so that the source material 16 emits positrons $e^+$. After being bombarded with photons 14, the source material 16 is then placed adjacent the specimen 18 to be tested. The specimen 18 is exposed at least some of the positrons $e^+$ emitted by the source material 16. Annihilation gamma rays $\gamma_a$ resulting from the annihilation within the specimen 18 of positrons $e^+$ with electrons $e^-$ are then detected by the detector 20 and processed by the processing system 22. As mentioned above, the measured annihilation energy plus or minus the momenta of the electrons and positrons provides a measure of the defect density or microcracking that may be present in the specimen 18.

The output data 26 from the processing system 22 may comprise any of a wide range of data derived from the detection of the annihilation gamma rays $\gamma_a$. For example, the momentum of the positron $e^+$ is related to the environment in which it resides. However, the positron thermalizes to a very low momentum state and interacts with electrons having momenta determined by the defect level and microstructure of the specimen 18 being tested. Electron momentum is relatively low in defects (e.g., microcracks in composite materials and polymers) or in large lattice structures, whereas electron momentum is higher in defect-free or tight lattice structures. The momentum of the positron/electron ($e^+/e^-$) interaction may be measured from the degree of broadening of the 511 keV gamma-ray energy peak caused by a number annihilation events. Alternatively, the momentum of the positron $e^+$ may be derived from the deviation from 180° of the annihilation gamma rays. Additional information about the annihilation event may be detected and used to derive additional or supplemental information regarding the specimen being tested, such as the presence within the specimen of contaminants or pores. Accordingly, the detection of positrons and the products of annihilation events provide much information relating to defects and other characteristics of the specimen being tested.

One advantage of the non-destructive testing apparatus according to the present invention is that it provides an external source of comparatively high energy positrons (e.g., positrons having energies in a range of about 0.5 MeV to about 5 MeV). Such high-energy positrons can penetrate more deeply (e.g., up to several centimeters in some materials, such as low-density polymers) into a specimen being tested. Perhaps even more advantageously, the source material 16 may be "activated" to produce positrons over substantially the entirety of the source material 16. In other words, the source material 16 may become a "distributed positron source" or simply, "a distributed source" of positrons, thereby allowing a larger area of the specimen 18 to be exposed to positrons than would otherwise be the case with conventional external positron point sources. Still yet other advantages of the present invention may be realized if the source material 16 is "conformable," i.e., may be readily conformed or "molded" to the specimen being tested. So conforming or molding the source material 16 to the specimen 18 improves the ability to inject positrons more deeply into the specimen 18 and allows for a more even distribution of those positrons that do enter the specimen 18. For example, it has been discovered that a conformable source material producing higher energy positrons is more effective at bombarding the specimen with positrons, even where the specimen 18 contains surface contaminants, such as grease, that often inhibit the bombardment of the specimens with positrons produced by conventional external positron sources.

In addition, the source material 16 often may be readily placed at any convenient location on the specimen 18. For example, in addition to being placed adjacent a front surface or portion of a specimen 18, the source material 16 could also be placed adjacent some other surface or portion of the specimen 18, such as a back surface or a side surface. In addition, measurements of the annihilation gamma rays may be made from any of a wide range of positions around the specimen 18, further increasing utility. Moreover, such measurements of the annihilation gamma rays may even be made where an intervening material (e.g., up to several centimeters of steel) might be located between the specimen 18 and the detector system 20. The ability to place the source material 16 adjacent any convenient portion of the specimen 18, as well as the ability to detect annihilation gamma rays, even where an intervening material exists, allows the present invention to be readily used on complex, fabricated structures, such as aircraft structures, without the need to disassemble the structure or remove material that might be located between the specimen 18 to be examined and the detector system 20.

Having briefly described one embodiment of a method and apparatus for non-destructive testing according to the present invention, as well as some of their more significant features and advantages, the various embodiments of the method and apparatus for non-destructive testing will now be described in detail.

Referring back now to FIG. 1, a first embodiment 10 of non-destructive testing apparatus according to the present invention may comprise a photon source 12 for producing photons 14 and directing the photons 14 toward the source material 16. It is generally preferred, but not required, that the photon source 12 be capable of producing photons 14 having user-selectable energies. The ability to vary the energies of the photons 14 will allow a user to "activate" (i.e., produce nuclei that emit positrons) source materials 16 comprising any of a wide range of elements by selecting the appropriate photon energies. The positrons are produced in such materials via a gamma-ray-capture or "gamma-n" reaction. For example, if the source material 16 comprises copper-63 ($^{63}Cu$), photons having energies of at least about 8 MeV will activate the copper-63 contained in the source material 16 by producing or forming within the source material 16 an isotope of copper (e.g., $^{64}Cu$) via the gamma ray capture or "gamma-n" reaction. $^{64}Cu$ is a "positron emitter." That is, $^{64}Cu$ emits positrons having energies of about 0.66 MeV during decay. $^{64}Cu$ has a half-life of about 12.7 hours. Similarly, photons having energies of at least about 11 MeV will convert $^{63}Cu$ to $^{62}Cu$ which emits higher energy positrons (i.e., positrons having energies of about 2.93 MeV) during decay. $^{62}Cu$ has a half-life of about 9.7 minutes.

Alternatively, if the ability to selectively activate certain elements contained in the source material 16 is not required or desired in a particular application, the photon source 12 need not be provided with capability to adjust the photon energy, but need only provide photons having energies sufficient to "activate" the source material 16 so that it emits positrons.

In one preferred embodiment having the ability to select the energies of the photons 14, the photon source 12 may comprise an electron accelerator 30 for producing a stream of accelerated electrons. In order to produce the photons 14 used to bombard the source material 16, the accelerated electrons are directed toward a target 32 which emits the photons 14 in response to bombardment by the accelerated electron stream produced by the electron accelerator 30. There is a correlation between the energies of the electrons comprising the electron stream produced by the accelerator 30 and the photons 14 produced by the target 32 in response to the electron bombardment. Consequently, photons 14 having specified maximum energies can be readily produced by selecting or adjusting the energies of the electrons contained in the electron stream produced by the accelerator 30.

In the embodiment shown and described herein, the photons 14 produced by the photon source 12 may be selected to have energies in the range of about 9 million electron volts (MeV) to about 21 MeV. Photons 14 having energies in this range are often referred to as high energy x-rays.

In accordance with the foregoing considerations, then, the electron accelerator 30 may comprise a linear accelerator of the type that are now known in the art or that may be developed in the future that are or would be suitable for the production of electrons having any of a wide range of energies. By way of example, in one preferred embodiment, the electron accelerator comprises a model 6000 linear accelerator available from Varian Corp. of Palo Alto, Calif. Alternatively, equivalent devices from the same or other manufacturers may also be used. The target 32 which emits the photons 14 may comprise tungsten, although other materials may also be used. Of course, the photon source 12 and/or the various components comprising the photon source 12 (e.g., the electron accelerator 30 and target 32) may be provided with suitable shielding materials (not shown), to prevent the unwanted escape of radiation from the photon source 12.

Figure 2:
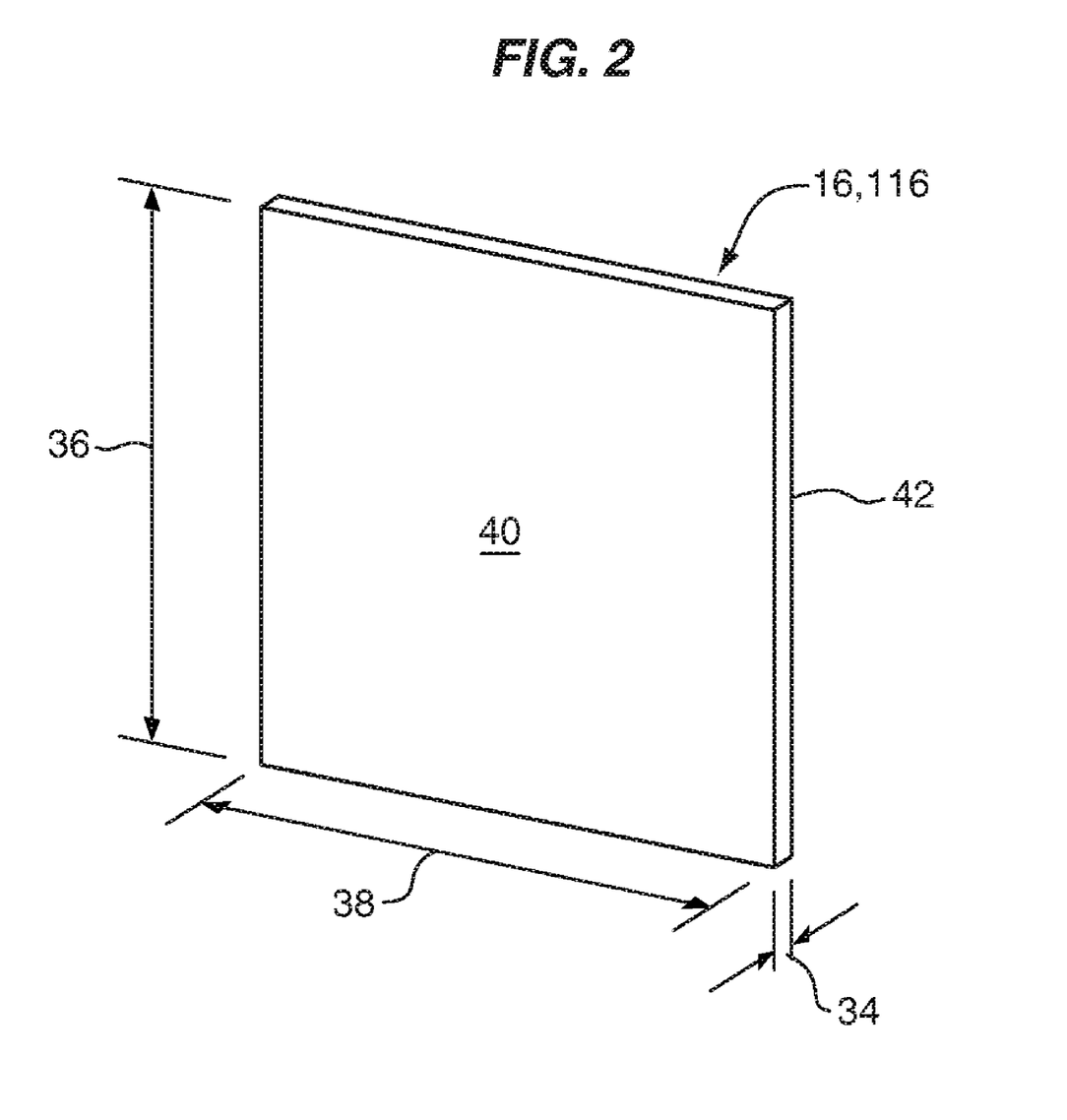
FIG. 2 is a perspective view of one embodiment of a source material.

The source material 16 is illustrated in FIGS. 1 and 2 and comprises a substance that emits positrons in response to bombardment by photons having the appropriate energies. The photon energy required to cause the source material 16 to emit positrons depends on the composition of the source material 16. For example, the source material 16 must contain at least one element that, when bombarded by photons, becomes an unstable isotope (e.g., via a "gamma-n" reaction) that decays in part by emitting positrons. Such an unstable isotope is referred to herein as a "positron emitter." A list of representative positron emitters, production reactions, the threshold photon (i.e., gamma ray) energies required to form or "activate" the positron emitters, as well as their half-lives, are presented herein as Table I. Table I may be used to readily identify representative isotopes that may be converted into positron emitters by photon bombardment, as well as to estimate the photon energies required to form the positron emitters. Stated simply, then, any material that contains at least one of isotopes presented in Table I or similar isotopes that produce positrons through photon or neutron interactions may be considered for use as the source material 16, although other considerations described herein and/or known to persons having ordinary skill in the art after becoming familiar with the teachings of the present invention may favor or disfavor its use in any particular application.

TABLE I

| Element | Reaction | Half-Life | Units | Threshold Energy MeV |
|---|---|---|---|---|
| Chromium | $^{50}Cr \rightarrow ^{49}Cr$ | 42.3 | Minutes | 20.5 |
| Iron | $^{54}Fe \rightarrow ^{53}Fe$ | 8.51 | Minutes | 14 |
| Nickel | $^{58}Ni \rightarrow ^{57}Ni$ | 35.6 | Hours | 12 |
| Copper | $^{65}Cu \rightarrow ^{64}Cu$ | 12.7 | Hours | 8 |
| Copper | $^{63}Cu \rightarrow ^{62}Cu$ | 9.74 | Minutes | 11 |
| Zinc | $^{64}Zn \rightarrow ^{63}Zn$ | 38.5 | Minutes | 20.45 |
| Zirconium | $^{90}Zr \rightarrow ^{89}Zr$ | 4.18 | Minutes | 12.3 |
| Molybdenum | $^{92}Mo \rightarrow ^{91}Mo$ | 1.08, 15.5 | Minutes | 12.5 |
| Tin | $^{112}Sn \rightarrow ^{111}Sn$ | 35 | Minutes | 12.5 |
| Antimony | $^{121}Sb \rightarrow ^{120}Sb$ | 15.9 | Minutes | 10 |
| Titanium | $^{46}Ti \rightarrow ^{45}Ti$ | 3.1 | Hours | 13 |
| Carbon | $^{12}C \rightarrow ^{11}C$ | 20.3 | Minutes | 19 |
| Nitrogen | $^{14}N \rightarrow ^{13}N$ | 9.97 | Minutes | 10.5 |
| Oxygen | $^{15}O \rightarrow ^{14}O$ | 122.2 | Seconds | ND |
| Fluorine | $^{19}F \rightarrow ^{18}F$ | 1.83 | Hours | 20 |
| Phosphorus | $^{31}P \rightarrow ^{30}P$ | 2.5 | Minutes | 10.9 |
| Chlorine | $^{35}Ci \rightarrow ^{34}Ci$ | 32.2 | Minutes | ND |
| Potassium | $^{39}K \rightarrow ^{38}K$ | 7.6 | Minutes | 12.5 |
| Gallium | $^{69}Ga \rightarrow ^{68}Ga$ | 1.13 | Hours | ND |
| Selenium | $^{74}Se \rightarrow ^{73}Se$ | 40 | Minutes | 12 |
| Bromine | $^{79}Br \rightarrow ^{78}Br$ | 6.45 | Minutes | ND |
| Ruthenium | $^{96}Ru \rightarrow ^{95}Ru$ | 1.64 | Hours | ND |
| Palladium | $^{102}Pd \rightarrow ^{101}Pd$ | 8.4 | Hours | ND |
| Silver | $^{107}Ag \rightarrow ^{106}Ag$ | 24 | Minutes | 9.0 |
| Cadmium | $^{106}Cd \rightarrow ^{105}Cd$ | 55.5 | Minutes | ND |
| Indium | $^{113}In \rightarrow ^{112}In$ | 14.4 | Minutes | ND |
| Xenon | $^{124}Xe \rightarrow ^{123}Xe$ | 2 | Hours | ND |
| Cerium | $^{136}Ce \rightarrow ^{135}Ce$ | 17.7 | Minutes | ND |
| Praseodymium | $^{141}Pr \rightarrow ^{140}Pr$ | 40 | Minutes | 7 |
| Neodymium | $^{142}Nd \rightarrow ^{141}Nd$ | 1.04 | Minutes | 9.5 |
| Samarium | $^{144}Sm \rightarrow ^{143}Sm$ | 8.83 | Minutes | 12.5 |
| Europium | $^{151}Eu \rightarrow ^{150}Eu$ | 12.8 | Hours | ND |
| Erbium | $^{164}Er \rightarrow ^{163}Er$ | 1.25 | Hours | ND |

It is also generally preferred, but not required, that the source material 16 comprise a flexible material so that it may be conformed or shaped to the particular specimen 18 being tested. As already mentioned, the ability to conform or shape at least a portion the source material 16 to at least a portion of the specimen 18 may provide certain advantages. Generally speaking, source materials 16 comprising thin metal sheets or "foils" containing at least one isotope that can be "photon activated" will result in highly-suitable source materials 16.

The thickness 34 (FIG. 2) of the sheet or foil is not particularly critical, and may comprise any of a range of thicknesses. However, if high-conformability is desired, then the thickness 34 of the source material 16 should be selected to provide the source material 16 with the desired degree of flexibility or conformability. For example, in one embodiment, the source material 16 comprises a copper sheet or foil having a thickness 34 in the range of about 0.25 mm to about 1 mm (0.025 mm to 0.1 mm preferred).

The sheet-like or foil source material 16 need not comprise any particular shape or configuration. Indeed, the source material 16 may comprise any of a wide range of shapes or configurations (e.g., rectangular, square, elliptical, tubular, or irregular) that may be required or desired for the particular application, as would be obvious to persons having ordinary skill in the art after having become familiar with the teachings of the present invention. Consequently, the present invention should not be regarded as limited to a source material 16 having any particular shape or configuration. However, by way of example, in one preferred embodiment, the source material 16 may comprise a generally square configuration, as illustrated in FIG. 2, having a length 36 that is substantially equal to a width 38. In the embodiment illustrated in FIG. 2, both the length 36 and width 38 are about 10 cm. That is, the source material 16 comprises a sheet or "coupon" of square foil having a total surface area of about 200 $cm^2$ (i.e., about 100 $cm^2$ for each side or face 40, 42 of the source material 16). Alternatively, source materials 16 having other surface areas may be used. By way of example, source materials 16 having single-side surface areas ranging from about 0.1 $cm^2$ to about 100 $cm^2$ have been used with good results.

In the embodiment shown and described in FIG. 1, the copper foil source material 16 comprises primarily $^{63}Cu$. With reference to Table I, $^{63}Cu$ may be "activated" or transformed into a positron emitter by bombarding the $^{63}Cu$ with photons having energies of at least about 8 MeV. Bombarding the copper foil with photons having at least this energy will result in the production of $^{64}Cu$ which is a positron emitter. That is, $^{64}Cu$ emits positrons having energies of about 0.66 MeV in the decay process. $^{64}Cu$ has a half-life of about 12.7 hours. Alternatively, higher energy photons, e.g., photons having energies of at least about 11 MeV, will result in the formation of $^{62}Cu$, which is also a positron emitter. $^{62}Cu$ emits positrons having energies of about 2.93 MeV. $^{62}Cu$ has a half-life of about 9.7 minutes.

It is generally preferable to "activate" as large a portion of the source material 16 as possible in order to provide an activated source material 16 that emits positrons $e^+$ over as wide an area as possible, depending on the application. Of course, the nature of the particular application may allow a smaller area of the source material 16 to be activated. For example, if the source material 16 comprises a surface area (i.e., size) that is larger than the size or surface area of the specimen 18 to be examined, then it may be desirable to only activate an area of the source material 16 that approximates the area of the specimen 18 to be examined. The activated area of the source material 16 should then be aligned with (e.g., positioned over) the corresponding area on the specimen 18 that is to be tested. In any event, the arrangement of the photon source 12 and the source material 16 should be such that substantially the entirety, or desired portion, as the case may be, of the source material 16 is exposed to photons 14 from the photon source 12.

The exposure of the source material 16 to photons 14 from the photon source 12 may be accomplished in any of a variety of ways. For example, if the photon source 12 produces a wide photon "beam" it may be that the area of the wide photon beam is sufficient to activate substantially the entirety (or desired portion) of the source material 16. Alternatively, the source material 16 may be moved with respect to the beam of photons 14 produced by the photon source 12 so that substantially the entirety (or desired portion) of the source material 16 is activated by the beam of photons 14. The relative movement may be regular (e.g., such as in a "raster" scan) or random. In any event, suitable movement apparatus 44 (FIG. 1) may be used to move the source material 16 with respect to the photon source 12. However, because apparatus for moving the source material 16 with respect to the photon source 12 could be easily provided by persons having ordinary skill in the art after having become familiar with the teachings of the present invention, the particular apparatus, such as movement apparatus 44, that may be used to expose substantially the entirety (or desired portion) of the source material 16 to the photons 14 from photon source 12 will not be described in further detail herein.

The detector system 20 may be positioned adjacent the specimen 18 so that the detector system 20 receives annihilation gamma rays $\gamma_a$ resulting from positron/electron annihilation events occurring within the specimen 18. Depending on the geometry of the particular installation, a shield (not shown) may be positioned between the photon source 12 and the detector system 20 to prevent gamma radiation from the photon source 12 from being detected by the detector system 20. However, in most cases, the photon source 12 will be far removed from the specimen 18 and/or inactive during the time the detector system 20 is detecting annihilation gamma rays $\gamma_a$. The detector system 20 may comprise any of a wide range of gamma ray detectors that are now known in the art or that may be developed in the future at are or would be suitable for detecting annihilation gamma rays $\gamma_a$ produced by the annihilation of positrons and electrons within the specimen 18. Accordingly, the present invention should not be regarded as limited to a detector system 20 comprising any particular type of gamma ray detector. However, by way of example, in one preferred embodiment, the detector 20 may comprise a germanium detector of the type that is well-known in the art and readily commercially available. Alternatively, the detector 20 could comprise a cadmium-zinc-tellurium or $BaF_2$ detector of the type that is also known in the art and readily commercially available.

It should also be noted that the detector system 20 should not be regarded as limited to a single detector. Indeed, depending on the type of processing algorithms utilized by the processing system 22 it may be desirable, or even required, that the detector system 20 comprise more than a single gamma ray detector. For example, while a Doppler broadening algorithm (described in greater detail below) that may be utilized by the processing system 22 will generally not require the use of two or more detectors, other algorithms, such as position locating algorithms, that may be implemented by the processing system 22 may require the use of at least two, and possibly several, gamma ray detectors 20 in order to determine the positions within the specimen 18 of the positron/electron annihilation events. However, since annihilation position determining techniques are well-known in the art, as are the requirements for the particular types and positions of detectors associated with such techniques, and since such multiple detectors could be easily provided by persons having ordinary skill in the art after having become familiar with the teachings of the present invention, the particular configurations of such multiple detector systems as they could be utilized in the present invention will not be described in greater detail herein.

The gamma ray detector (or detectors) comprising the detector system 20 may also be provided with a collimator 46 to collimate the annihilation gamma rays $\gamma_a$. The collimator 46 may comprise any of a wide range of collimators, such as, for example, a variable-slit type collimator, that are now known in the art or that may be developed in the future. However, because collimators are well-known in the art and could be readily provided by persons having ordinary skill in the art after having become familiar with the teachings of the present invention, the particular collimator 46 that may be used with the detector 20 will not be described in further detail herein.

The processing system 22 is operatively associated with the detector system 20 and receives output data 24 produced by the detector system 20. As mentioned above, the output data 24 produced by the detector system 20 may be processed in accordance with any of a wide variety of algorithms that are now known in the art or that may be developed in the future to allow the processing system 22 to produce output data 26 indicative of at least one material characteristic of the specimen 18 being tested. Algorithms that may be utilized by the data processing system include a Doppler broadening algorithm, such as the type disclosed in U.S. Pat. No. 6,178,218 issued to Akers, which is incorporated herein by reference for all that is disclosed. Other algorithms that may be utilized are disclosed in U.S. patent application Ser. No. 09/932,531, filed Aug. 17, 2001, and entitled "Apparatus for Photon Activation Positron Analysis," to Akers which is incorporated herein by reference for all that it discloses. In addition, algorithms suitable for use in positron annihilation are also disclosed in "Positron-Annihilation Spectroscopy", Encyclopedia of Applied Physics, Vol. 14, pp. 607-632 (1996), which is also incorporated herein by reference for all that it discloses. Because algorithms suitable for processing data related to the annihilation gamma rays detected by the detector system 20 are known in the at and could be easily provided by persons having ordinary skill in the art after having become familiar with the teachings of the present invention, the particular algorithm or algorithms that may be utilized by the processing system 22 will not be described in further detail herein.

The processing system 22 may comprise any of a wide range of systems or combinations of systems known in the art that would be suitable for collecting the output data 24 from the detector system 20 and for processing the output data 24 in accordance with the one or more algorithms described above. Therefore, the present invention should not be regarded as limited to processing systems 22 comprising any particular type or configuration. By way of example, in one embodiment, the processing system 22 comprises a general purpose programmable computer system, such as the ubiquitous personal computer. However, because such processing systems are well known in the art and could be easily provided by persons having ordinary skill in the art after becoming familiar with the teachings of the present invention and after considering the particular type or types of algorithms to be used to process the data 24 from the detector system 20 to produce the output data 26, the processing system 22 utilized in one preferred embodiment of the invention will not be described in further detail herein.

The processing system 22 may be connected to a suitable user interface 28, such as a flat-panel display (not shown), for displaying the output data 26 produced by the processing system 22. Alternatively, the processing system 22 could also provide the output data 26 in computer-readable form for subsequent display and/or manipulation by a device external to the processing system 22, such as a personal computer (not shown). However, because such user-interfaces are well-known in the art and could be easily provided by persons having ordinary skill in the art after having become familiar with the teachings provided herein and after considering the particular application, the present invention should not be regarded as limited to any particular type of user-interface 28.

A non-destructive testing method according to the present invention may comprise providing a source material 16 that will produce positrons $e^+$ in response to photon bombardment. In the embodiment shown and described in FIG. 1, the source material 16 comprises a thin sheet or foil "coupon" comprising $^{63}$Cu having a generally square configuration, substantially as illustrated in FIG. 2. More specifically, the copper source material 16 comprises a foil sheet having a thickness 34 of about 0.025 mm, a length 36 of about 10 mm and a width 38 of about 10 mm. The copper foil comprising the source material 16 is then positioned adjacent the photon source 12, which bombards the source material 16 with photons 14. As mentioned above, the source material 16 may be mounted on a suitable movement apparatus 44 which moves the source material 16 relative to the photons 14 from photon source 12 so that the desired portion of the source material 16 may be exposed to the photons 14.

Once the source material 16 is positioned adjacent the photon source 12, the photon source 12 may then be operated so that the photons 14 produced thereby have energies in the range of about 9 MeV to about 21 MeV. Photons 14 of such energies are sufficient to activate the source material 16, causing it to produce positrons $e^+$ in the manner already described.

The time required to activate the source material 16 will vary depending on the size of the source material 16 that is to be used in a particular application, as well as on other factors, as would become apparent to persons having ordinary skill in the art after having become familiar with the teachings provided herein and after considering the particular devices and materials being used. Consequently, the present invention should not be regarded as limited to exposing the source material 16 to photons 14 for any particular time. However, by way of example, in one preferred embodiment, the source material 16 is exposed to the photons 14 from the photon source 12 for a time in the range of about 0.5 to about 3 minutes, which is sufficient to activate substantially the entirety of the source material 16 in the embodiment shown and described herein.

After being activated, the source material 16 may then be removed from its position adjacent the photon source 12 and positioned adjacent the specimen 18 to be tested. Generally speaking, it will be advantageous to place the source material 16 in direct contact with the specimen 18. If the specimen 18 comprises an irregularly shaped body and if the source material 16 comprises a conformable material, then it also will be advantageous to conform or mold the source material 16 to the specimen 18, as best seen in FIG. 1. So conforming or molding the source material 16 to the specimen 18 is readily accomplished in the embodiment illustrated in FIG. 1, wherein the source material 16 comprises copper foil.

When so positioned adjacent the specimen 18, positrons $e^+$ emitted by the activated source material 16 bombard the specimen 18. In many embodiments, the positrons $e^+$ will have energies (e.g., in the range of about 2 MeV to about 5 MeV) greater than those normally associated with conventional external positron sources (e.g., about 0.5 MeV), thus will generally penetrate the specimen 18 to a greater depth. The source material 16 may be left in place adjacent the specimen 18 for a time sufficient to allow the detector system 20 to collect an amount of annihilation gamma rays $\gamma_a$ sufficient to allow the processing system 22 to produce output data 26. In this regard, it should be noted that the amount of annihilation gamma rays $\gamma_a$ needed to be detected by the detector system 20 will vary depending on a wide variety of factors, such as, for example, the sensitivity of the detector system 20, the particular algorithms utilized by the processing system 22, as well as on other factors that would be appreciated by persons having ordinary skill in the art. Therefore, the present invention should not be regarded as limited to any particular times. However, by way of example, in one embodiment, the source material 16 is positioned adjacent the specimen for a time in the range of about 3 minutes to about 10 minutes.

The source material 16 may be left in place during the data collection (i.e., detection) process. Alternatively, the source material 16 may be removed before conducting the data collection process. In one embodiment wherein the source material 16 is left in place, the source material 16 is placed on the side of the specimen 18 that is opposite the detector assembly 20. Alternatively, the source material 16 may be placed on the same side as the detector assembly 20. In this case, it may be desirable to provide the detector assembly 20 with suitable shielding (e.g., a cover foil) to prevent the positrons emitted by the source material 16 from interfering with the detector assembly 20.

Figure 3:
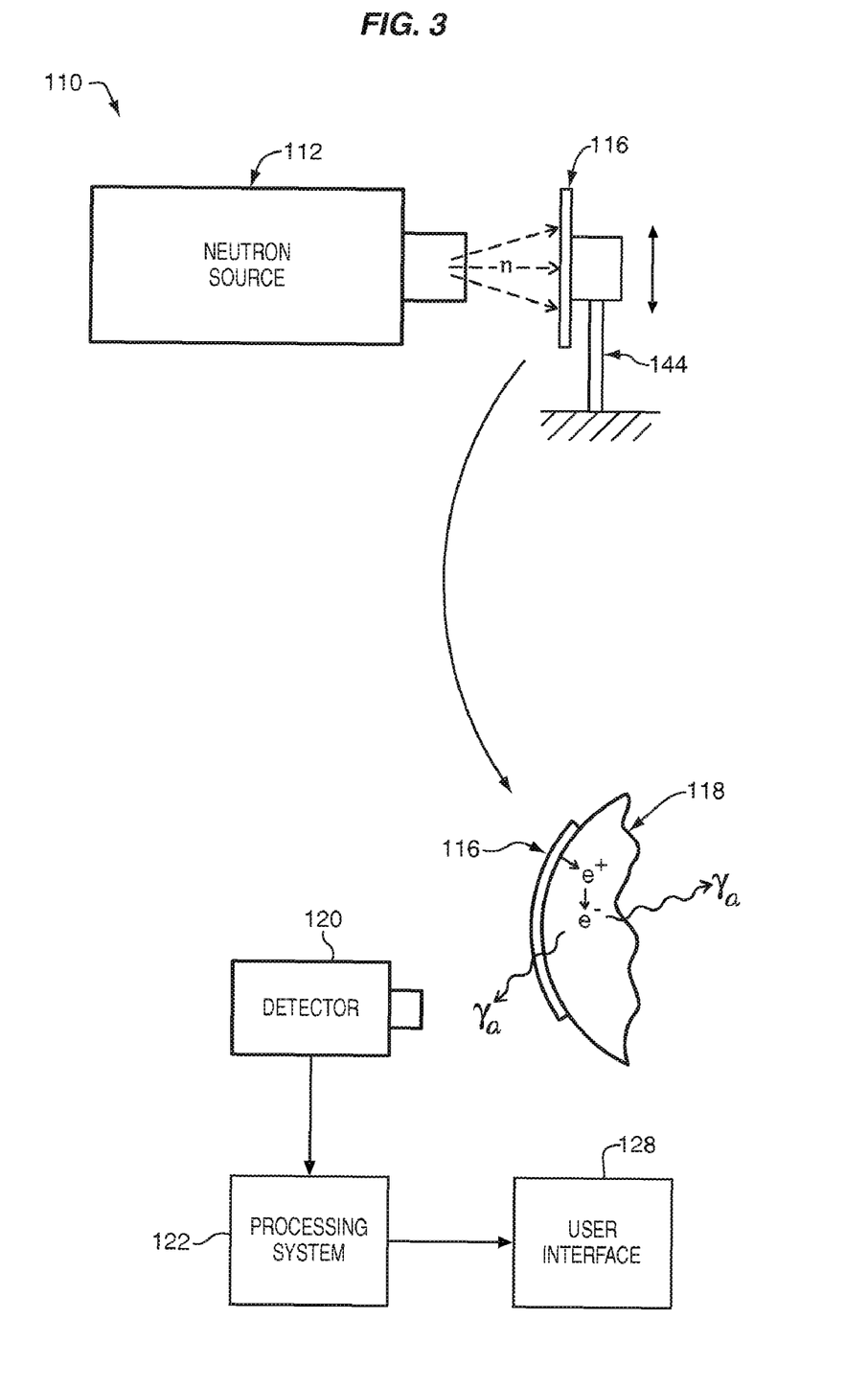
FIG. 3 is a schematic representation of another embodiment of non-destructive testing apparatus according to the present invention.

Another embodiment 110 of non-destructive testing apparatus according to the present invention is illustrated in FIG. 3. The second embodiment 110 differs from the first embodiment 10 in that the second embodiment 110 involves the activation of a source material 116 by neutrons n instead of photons 14. The neutrons n may be produced by a suitable neutron source 112. It is generally preferred, but not required, that the neutron source 112 be capable of producing neutrons n having energies of about 14 MeV. Alternatively, the neutron source 112 could comprise a neutron source capable of producing neutrons having user-selectable energies. The ability to vary the energies of the neutrons n will allow a user to activate (i.e., cause to emit positrons) source materials 116 comprising various elements by selecting the appropriate neutron energies. The positrons are produced in such materials via either an (n,2n) reaction or an (n,γ) reaction. Materials capable of producing positrons $e^+$ in response to neutron bombardment include many of those produced using photons. It is generally preferred that the neutron source 112 produce neutrons n having energies of up to about 14 MeV for (n,2n) reactions. Alternatively, lower energy neutrons can be used for other reactions.

It should be noted that neutrons n from the neutron source 112 may activate other materials within the source material 116, causing them to become positron emitters through the process of pair production. However, this only happens of the energies of the prompt gamma rays (emitted during pair production) exceed about 1.1 MeV. Prompt gamma rays having energies less than about 1.1 MeV typically result in the production of delayed gamma rays and, occasionally, electrons, but not positrons.

The neutron source 112 may comprise any of a wide range of devices suitable for producing neutrons having sufficient energies to activate the source material 116. By way of example, in one preferred embodiment, the neutron source 112 comprises a model no. A-320 neutron source available from the MF Physics Corporation of a subsidiary of the Thermo Electron Corporation. Alternatively, the neutron source 112 could comprise an isotopic source, such as $^{252}$Cf.

The source material 116 comprises a substance that emits positrons in response to bombardment by neutrons having the appropriate energies. The neutron energy required to cause the source material 116 to emit positrons depends on the composition of the source material 116. That is, the source material 116 must contain at least one element that, when bombarded by neutrons, becomes an unstable isotope that decays in part by emitting positrons. The neutron energies required to activate certain elements are known, thus will not be provided herein. However, by way of example, if the source material 116 comprises $^{63}$Cu, bombardment of the source material 116 by neutrons n having energies of about 14 MeV will result in the production of $^{64}$Cu via the (n–γ) reaction process. $^{64}$Cu is a "positron emitter" (i.e., decays by emitting positrons) having a half-life of about 12.7 hours. Also, the $^{63}$Cu (n,2n) reaction produces $^{62}$Cu, a positron emitter having a half-life of 9.7 minutes. Stated simply, then, any material that contains at least one element that is capable of becoming a positron emitter in response to neutron bombardment may be selected as the source material 116. For example, suitable source materials 116 may comprise copper and various alloys thereof, as well as many aluminum and steel alloys.

As was the case for the source material 16, it is generally preferred, but not required, that the source material 116 comprise a flexible material so that it may be conformed or shaped to the particular specimen 118 being tested. As discussed above, the ability to conform or shape at least a portion the source material 116 to at least a portion of the specimen 118 may provide certain advantages. Generally speaking, source materials 116 comprising thin metal sheets or "foils" containing at least one isotope that can be "neutron activated," such as copper, as well as certain aluminum and steel alloys, will result in highly-suitable source materials 116. With reference back now to FIG. 2, the thickness 34 of the sheet or foil is not particularly critical, any may comprise any of a range of thicknesses, although the sensitivity is greater with thinner source materials. However, if high-conformability is desired, then the thickness 34 of the source material 116 should be selected to provide the source material 116 with the desired degree of flexibility or conformability. For example, in one embodiment, the source material 116 comprises a copper sheet or foil having a thickness 34 in the range of about 0.025 mm to about 1 mm (0.025 mm to 0.1 mm preferred).

The sheet-like or foil source material 116 need not comprise any particular shape or configuration. Indeed, the source material 116 may comprise any of a wide range of shapes or configurations (e.g., rectangular, square, elliptical, or irregular) that may be required or desired for the particular application, as would be obvious to persons having ordinary skill in the art after having become familiar with the teachings of the present invention. Consequently, the present invention should not be regarded as limited to a source material 116 having any particular shape or configuration. However, by way of example, in one preferred embodiment, the source material 116 may comprise a generally square configuration, as illustrated in FIG. 2, having a length 36 substantially equal to a width 38, both of which are about 10 cm to yield a total surface area of about 200 cm$^2$ (e.g., 100 cm$^2$ for each side or face 40, 42 of the source material 116). However, and as mentioned above, source materials having single side surface areas in the range of about 0.1 cm$^2$ to about 100 cm$^2$ may be used as well.

In the embodiment shown and described in FIG. 3, the copper foil source material 116 comprises primarily $^{63}$Cu. $^{63}$Cu may be "activated" or caused to emit positrons by bombarding it with neutrons having energies of at least about 14 MeV. Bombarding the copper foil with neutrons having at least this energy will result in the formation or production of $^{64}$Cu (e.g., via the (n,γ) reaction) and $^{62}$Cu (e.g., via the (n,2n) reaction), both of which emit positrons in the decay process.

As was the case for the first embodiment, it is generally preferable to "activate" as large a portion of the source material 116 as possible in order to provide an activated source material 116 that emits positrons e$^+$ over as large an area as possible, or in a size to produce the desired resolution for a particular measurement. Of course, the particular application may allow a smaller area of the source material 116 to be activated. For example, if the source material 116 comprises a surface area (i.e., size) that is larger than the size or surface area of the specimen 118 to be examined, then it may be desirable to only activate an area of the source material 116 that approximates the area of the specimen 118 to be examined. The activated area of the source material 116 should then be aligned with (e.g., positioned over) the corresponding area on the specimen 118 that is to be tested. In any event, the arrangement of the neutron source 112 and the source material 116 should be such that substantially the entirety, or desired portion, as the case may be, of the source material 116 is exposed to neutrons n from the neutron source 112.

The exposure of the source material 116 to neutrons n from the neutron source 112 may be accomplished in any of a variety of ways. For example, if the neutron source 112 produces a wide neutron "beam" it may be that the area of the wide neutron beam is sufficient to activate substantially the entirety (or desired portion) of the source material 116. Alternatively, the source material 116 may be moved with respect to the neutron beam produced by the neutron source 112 so that substantially the entirety (or desired portion) of the source material 116 is activated by the beam of neutrons. The relative movement may be regular (e.g., such as in a "raster" scan) or random. In any event, suitable movement apparatus 144 may be used to move the source material 116 with respect to the neutron source 112.

The non-destructive testing apparatus 110 may also be provided with a detector system 120, a processing system 122, as well as a user interface 128. These systems may be in every respect identical to the corresponding systems already described for the first embodiment 10 and illustrated in FIG. 1. Consequently, the detector system 120, processing system 122, and user interface 128 that may be utilized in one embodiment of the apparatus 110 will not be described in further detail herein.

Another non-destructive testing method according to the present invention may comprise providing a source material 116 that will produce positrons e$^+$ in response to neutron bombardment. In the embodiment shown and described in FIG. 3, the source material 116 comprises a thin sheet or foil comprising $^{63}$Cu having a generally square configuration, substantially as illustrated in FIG. 2. More specifically, the copper source material 116 comprises a foil sheet having a thickness 34 of about 0.1 mm, a length 36 of about 10 mm and a width 38 of about 10 mm. The copper foil comprising the source material 116 is then positioned adjacent the neutron source 112, which bombards the source material 116 with neutrons n. As mentioned above, the source material 116 may be mounted on a suitable movement apparatus 144 which moves the source material 116 relative to the neutrons n from neutron source 112 so that the desired portion of the source material 116 is exposed to the neutrons n.

Once the source material 116 is positioned adjacent the neutron source 112, the neutron source 112 may then be operated so that the neutrons n produced thereby have energies of about 14 MeV. Neutrons n of such energies are sufficient to activate the copper atoms in the source material 116, causing it to produce positrons e$^+$ in the manner already described.

The time required to activate the source material 116 will vary depending on the size of the source material 116 that is to be used in a particular application, as well as on other factors, as would become apparent to persons having ordinary skill in the art after having become familiar with the teachings provided herein and after considering the particular devices and materials being used. Consequently, the present invention should not be regarded as limited to exposing the source material 116 to neutrons n for any particular time. However, by way of example, in one preferred embodiment, the source material 116 is exposed to the neutrons n from the neutron source 112 for a time in the range of about 1 to about 20 minutes, which was sufficient to activate substantially the entirety of the source material 116.

After being activated, the source material 116 may then be removed from its position adjacent the neutron source 112 and positioned adjacent the specimen 118 to be tested. Generally speaking, it will be advantageous to place the source material 116 in direct contact with the specimen 118. If the specimen 118 comprises an irregularly shaped body and if the source material 116 comprises a conformable material, then it also will be advantageous to conform or mold the source material 16 to the specimen 118, as illustrated in FIG. 3. So conforming or molding the source material 116 to the specimen 118 is readily accomplished in the embodiment illustrated in FIG. 3, wherein the source material 116 comprises copper foil.

When so positioned adjacent the specimen 118, positrons $e^+$ emitted by the activated source material 116 bombard the specimen 118. In many embodiments, the positrons $e^+$ will have energies greater than those normally associated with conventional external positron sources, thus will generally penetrate the specimen 118 to a greater depth. The source material 116 may be left in place adjacent the specimen 118 for a time sufficient to allow the detector system 120 to collect an amount of annihilation gamma rays $\gamma_a$ sufficient to allow the processing system 122 to produce output data 126. Because the amount of annihilation gamma rays $\gamma_a$ needed to be detected by the detector system 120 will vary depending on a wide variety of factors, such as, for example, the sensitivity of the detector system 120, the particular algorithms utilized by the processing system 122, as well as on other factors that would be appreciated by persons having ordinary skill in the art, the present invention should not be regarded as limited to any particular times. However, by way of example, in one embodiment, the source material 116 is positioned adjacent the specimen for a time in the range of about 3 minutes to about 60 minutes.

Having herein set forth preferred embodiments of the present invention, it is anticipated that suitable modifications can be made thereto which will nonetheless remain within the scope of the invention. The invention shall therefore only be construed in accordance with the following claims:

The invention claimed is:

1. Non-destructive testing apparatus, comprising:
a photon source;
a source material configured to emit positrons in response to bombardment of said source material with photons from said photon source, said source material being positionable adjacent a specimen, so that the specimen is exposed to at least some of the positrons emitted by said source material, the specimen emitting annihilation gamma rays in response to exposure to the at least some of the positrons emitted by said source material, said source material comprising material in a solid state and being conformable so that at least a portion of said source material may be conformed to at least a portion of the specimen; and
a detector system configured to detect annihilation gamma rays emitted by the specimen and being positionable adjacent the specimen.

2. The non-destructive testing apparatus of claim 1, wherein said source material has a surface area in the range of about 0.1 cm$^2$ to about 100 cm$^2$.

3. The non-destructive testing apparatus of claim 1, wherein said photon source produces photons having energies in a range of about 9 MeV to about 21 MeV.

4. The non-destructive testing apparatus of claim 1, wherein said source material emits positrons having energies in a range of about 0.5 MeV to about 5 MeV.

5. Non-destructive testing apparatus, comprising:
photon source means for producing photons;
source material means for emitting positrons in response to bombardment of said source material means with photons and for being positionable adjacent a specimen so that the specimen is exposed to at feast some of the positrons emitted by said source material means, and said source material means comprising matter in a solid state for conforming at least a portion of said source material means to at least a portion of the specimen; and
detector means positioned adjacent the specimen for detecting annihilation gamma rays emitted by the specimen.

* * * * *